United States Patent [19]

Huchzermeier et al.

[11] Patent Number: 4,476,228

[45] Date of Patent: Oct. 9, 1984

[54] DETERMINATION OF UNSATURATED THYROXINE BINDING PROTEIN SITES USING FLUORESCENCE POLARIZATION TECHNIQUES

[75] Inventors: Roy F. Huchzermeier, Lake Villa; Thomas G. Spring, Highland Park, both of Ill.

[73] Assignee: Abbott Laboratories, North Chicago, Ill.

[21] Appl. No.: 440,068

[22] Filed: Nov. 8, 1982

[51] Int. Cl.$^3$ ..................... G01N 3/52; C07D 311/82
[52] U.S. Cl. .................................. 436/500; 436/537; 436/546; 436/800; 549/223
[58] Field of Search ..................... 936/500, 537, 546; 549/800, 223

[56]  References Cited

U.S. PATENT DOCUMENTS

| | | | |
|---|---|---|---|
| 4,161,515 | 7/1979 | Ullman | 424/8 |
| 4,347,058 | 8/1982 | Polito et al. | 436/500 |
| 4,347,059 | 8/1982 | Polito et al. | 436/500 |

FOREIGN PATENT DOCUMENTS

| | | | |
|---|---|---|---|
| 15695 | 9/1980 | European Pat. Off. | 436/500 |
| 3205506 | 9/1982 | Fed. Rep. of Germany | 436/500 |
| 2487835 | 2/1982 | France | 436/500 |

OTHER PUBLICATIONS

Maratsugu et al., Chem. Abstracts, vol. 97 (1982) #175226h.

Primary Examiner—Christine M. Nucker
Attorney, Agent, or Firm—James L. Wilcox

[57]  ABSTRACT

This invention encompasses a method for measuring unsaturated thyroxine binding protein sites in a sample comprising intermixing with the sample an effective amount of fluorescent labeled tracer having binding affinity for thyroxine binding proteins and then measuring the amount of tracer bound to the thyroxine binding protein using fluorescence polarization techniques.

10 Claims, No Drawings

DETERMINATION OF UNSATURATED THYROXINE BINDING PROTEIN SITES USING FLUORESCENCE POLARIZATION TECHNIQUES

BACKGROUND OF THE INVENTION

Free thyroxine is the generally accepted marker for the initial assessment of possible thyroid dysfunction: *J. Clin. Invest.*, 45:133, 1966. Since approximately 0.05% of the total circulating thyroxine is physiologically active (i.e., free thyroxine), it is apparent that measurement of total thyroxine concentration only is not a completely satisfactory marker. Free thyroxine is however difficult to measure directly: Berger, S., and Quinn, J. L., *Fundamentals of Clinical Chemistry*, Tietz, N. W., Ed; W. B. Saunders, Co.: Philadelphia, 1976, Chapter 14 and Robbins, J., *Thyroid Hormone Metabolism*, Harlem and Orr, Ed., 1975, Chapter 1. The remaining circulating thyroxine is bound to protein, primarily thyroxine binding globulin (TBG): Robbins, J., and Rall, J. G., Proteins Associated with Thyroid Hormones, *Physiol. Rev.*, 40, 415, 1960. Thus, the measurement of total circulating thyroxine concentration and of thyroxine binding globulin concentration provides a good assessment of the relative concentration of free thyroxine.

Various methods have been used to assess the level of thyroxine binding globulin concentrations. The oldest method is the $T_3$ uptake study which measures unsaturated thyroxine binding globulin capacity: *J. Clin. Endocrinol.*, 17:33, January, 1957 and *J. Clin. Endocrinol.*, 25:39–54, 1965. $T_3$ uptake assays use $^{125}I$ labeled liothyronine ($T_3$) to competitively bind to the free TBG sites and a secondary solid support (viz: resin, charcoal, etc.). After an incubation period and suitable separation technique (vis: washing, centrifugation, etc.) the remaining radioactivity on the solid support is counted. This radioactivity is inversely proportional to the unsaturated thyroxine binding globulin concentration.

Another methodology is a radioimmunoassay which utilizes antibody specific for thyroxine binding globulin. However methodology does not measure the binding ability of the thyroxine binding globulins: *Clin. Chem. Acta.*, 87, (1978), 373–381.

A third methodology assesses the total thyroxine binding globulin capacity by equilibrating with a large excess of thyroxine to displace the endogenous thyroxine in the sample: U.S. Pat. No. 3,960,492 (1976).

Another methodology utilizes a thyroxine irreversible enzyme inhibitor conjugate, which binds by way of the thyroxine moiety of a site of unsaturation on the thyroxine binding globulin, thereby inactivating the irreversible enzyme inhibitor moiety. Thus, the greater the amount of unsaturated thyroxine binding globulin, the more conjugate that will be bound and the amount of irreversible enzyme inhibitor which will be available to inhibit the enzyme will be reduced. That is: increased amounts of thyroxine binding globulin will result in greater enzyme activity. Thus, intermixing enzyme and substrate to the enzyme and the above-described thyroxine irreversible enzyme inhibitor with serum permits determination of unsaturated thyroxine binding globulin in serum: U.S. Pat. No. 4,341,865.

Another methodology involves the use of fluorescent polarization immunoassay techniques to measure $T_3$ uptake. However, this procedure involves separation steps as well as the use of antibody against $T_3$: U.S. Pat. No. 4,347,059.

It is known that thyroxine will bind to binding proteins other than thyroxine binding protein, in particular, albumin and pre-albumin and therefore the presence of such proteins will influence free thyroxine levels. Fesco, et al, *Clin. Chem.*, 28/6, p. 1325–1329 (1982).

SUMMARY OF THE INVENTION

The present invention relates to a method for determining unsaturated thyroxine binding protein sites utilizing fluorescent polarization techniques. In particular the present invention relates to a method for determining unsaturated thyroxine binding protein sites comprising contacting a sample containing thyroxine binding proteins, with a fluorescent labeled tracer wherein said fluorescent labeled tracer has a preferential binding affinity for thyroxine binding globulin, and the measuring the amount of fluorescent labeled tracer bound to thyroxine binding proteins utilizing fluorescent polarization techniques as a measure of unsaturated thyroxine binding protein sites.

The measurement of unsaturated thyroxine binding protein sites is used in conjunction with total thyroxine concentration to determine a free thyroxine index which is a generally accepted marker for the initial assessment of thyroid dysfunction.

DETAILED DESCRIPTION OF THE INVENTION

Samples which can be assayed by the present invention for the determination of unsaturated thyroxine binding protein sites include biological fluids having either an unknown T uptake (e.g., a patient's sample) or biological fluids having a known T uptake (i.e., standards). Typical biological fluids include, but are not limited to plasma and serum. Serum is the preferred biological fluid employed in the analysis of the present invention.

As used herein the term "T uptake" refers to the relative concentration of unsaturated thryoxine binding protein sites available for binding to thyroxine.

The fluorescent labeled tracers which are utilized in the methods of the present invention preferentially bind thyroxine binding globulin rather than other specific binding proteins. The term "preferential binding affinity for thyroxine binding globulin" refers to the fact that the tracer has essentially the same relative binding affinity for thyroxine binding globulin, albumin and pre-albumin as does thyroxine. That is, the ratio of the relative assay response of a tracer to thryoxine binding globulin and the binding of the tracer to albumin and thyroxine binding pre-albumin should be greater than 1 and preferably greater than 3.

The fluorescent labeled tracers comprise a thyroxine moiety or thyroxine analog, bound to a fluorescent label. Any suitable fluorescent label can be used to label the thyroxine or thyroxine analog. Fluorescent labels include, but are not limited to, fluorescein and rhodamine and derivatives thereof. It is preferred to employ a fluorescein derivative as the fluorescent label. The fluorescent labeled tracers wherein a thyroxine moiety or thyroxine analog are bound to fluorescein or fluorescein derivatives are hereinafter referred to as thyroxine-fluorescein conjugates.

The following structures illustrate preferred thyroxine-fluorescein conjugates useful as tracers in conjunction with the methods of the present invention:

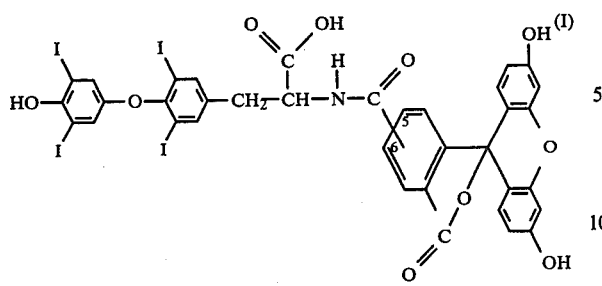

and biologically acceptable salts thereof, wherein the bonded carbonyl group is bonded to the 5 or 6 position on the fluorescein moiety; and

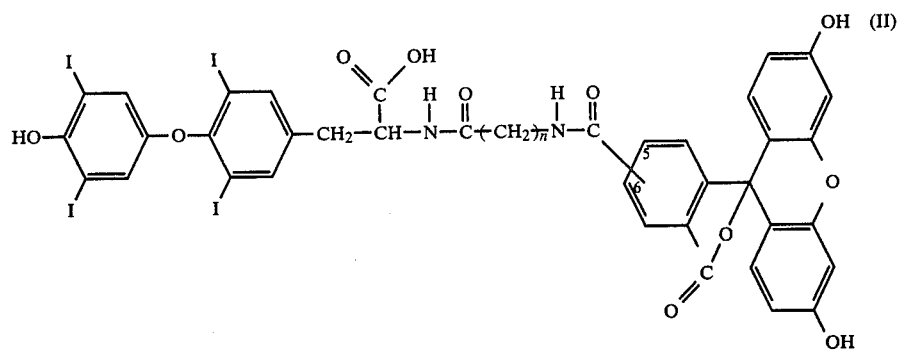

wherein n is an integer of from 1 to 8 and biologically acceptable salts thereof, and wherein the carbonyl group is bonded to the 5 or 6, position on the fluorescein moiety; and

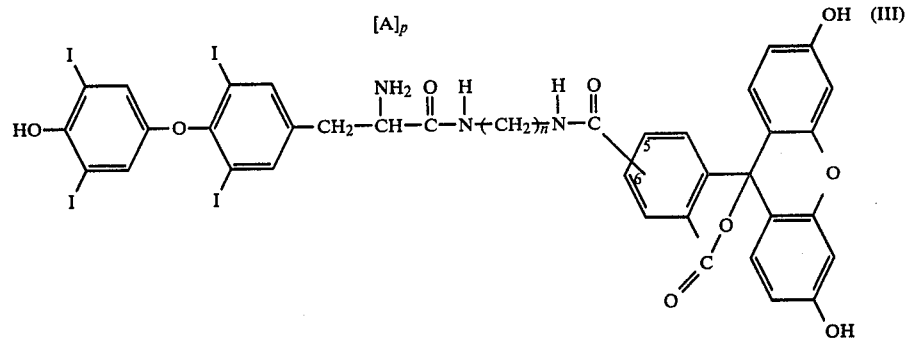

wherein m is an integer of from 1 to 8, p is an integer 0 or 1, A is an acid salt having a pH less than 3, such as, for example, hydrochloride, trifluoroacetate, trichloroacetate, acetate, and the like, and biologically acceptable salts thereofm and wherein the carbonyl group is bonded to the 5 or 6 position on the fluorescein moiety.

It is preferred to employ tracers of formula (II) and (III) wherein n or m is in a range of 2 to 4 and more preferred to employ tracers of formula (III) wherein n is 2 or 3. It is most preferred to employ a tracer of formula (III) wherein m is 3.

In accordance with the methods of the present invention a sample containing thyroxine binding protein is contacted with a fluorescent labeled tracer thus permitting the fluorescent labeled tracer to bind the unsaturated thyroxine binding protein sites in the sample and form a complex. The production of the complex increases the fluorescence polarization of the solution from that containing only free tracer. The increase in polarization of fluorescence caused by contacting the thyroxine binding protein with the fluorescent labeled tracer can be measured by known polarized fluorometric techniques via either an endpoint or kinetic methodology. Preferably, an endpoint fluorometric technique is employed in the assay of this invention.

To overcome problems associated with nonspecific tracer binding and variable background fluorescence, the sample must be treated with a composition comprising a nonfluorescent surfactant in a buffered medium having a pH greater than 7.0. Nonfluorescent surfactants utilized in such compositions are readily ascertained by one of ordinary skill in the art and include for example, sodium dodecyl sulfate. The buffered media utilized in such compositions include buffers sufficient to maintain the pH of the solution greater than pH 7 and preferably in the range of 7.5-9.5, and most preferably in the range of 8.0-9.0. Respective buffered media include bicarbonate buffers, tris(hydroxymethyl) aminomethane and the like. In addition, if a buffer having a low pK is employed, such as, a phosphate buffer, organic bases such as triethylamine and triethylenediamine may be employed in conjunction with a buffer to provide a buffered medium in the desired pH range.

The following examples serve to further illustrate the present invention.

EXAMPLE 1

T Uptake Fluorescence Polarization Assay

A. Reagents

1. Pretreatment Solution—A solution containing 0.15% sodium dodecyl sulfate 0.564M triethylenediamine (DABCO), and 0.1% sodium azide in 0.1M sodium phosphate buffer (pH 7.25).

2. T4 Fluorescein Tracer—A tracer of formula (III) wherein m=3 is employed at a concentration of $2.4 \times 10^{-7}$M in a buffered medium containing 0.005% sodium dodecyl sulfate, 0.1% bovine gamma globulin, and 0.1% sodium azide in 0.1M sodium phosphate buffer.

3. T Uptake Calibrators—Sheep anti-T antisera in a 4% human serum matrix having the following uptake values: 0, 0.5, 1.0, 1.5, 2.0, and 2.5. An uptake value of 1.0 is equivalent to the T uptake of normal serum.

4. Diluent buffer—0.1M sodium phosphate containing 0.1% bovine gamma globulin and 0.1% sodium azide.

All polarized fluorescence measurements were made using a polarization spectrofluorimeter (Abbott $TD_x$ ™ Fluorescence Polarization Analyzer.

B. Assay Protocol

1. To 1 μl aliquot of an unknown sample is added 25 μl of the pretreatment solution and the resulting mixture is diluted to 1 ml with diluent buffer. The resultant assay solution is mixed and the polarized fluorescence background is measured.

2. To the assay solution in Step 1. is added a second 1 μl aliquot of the unknown sample, 25 μl of the pretreatment solution 25 μl of $T_4$ fluorescein tracer, and the buffer to a final volume of 2 ml. The resultant solution is mixed and the polarized fluorescence is measured.

3. The fluorescence polarization due to tracer binding is obtained by subtracting the polarized fluorescence intensities of the background from the final polarized fluorescence intensities of the mixture.

4. The polarization values obtained are proportional to the T uptake of each sample.

5. The fluorescence polarization for a sample is cmopared to a standard curve prepared using calibrators of known T uptake values to indicate the T uptake value.

EXAMPLE 2

In order to evaluate the efficacy of the T uptake fluorescence polarization assay of the present invention, a correlation study was conducted employing (i) a radio-assay $T_3$ uptake procedure set forth in Trio-Bead $T_3$ Uptake Diagnostic Kit, Abbott Laboratories, North Chicago, Ill. and (ii) an enzyme inhibitor T uptake procedure set forth in Thyrozyme Uptake Diagnostic Kit, Abbott Laboratories, North Chicago, Ill.

The data obtained from the fluorescence polarization assay of the present invention, the radioassay and enzyme inhibitor assay are set forth in Table I.

TABLE I

| Sample | T UPTAKE | | |
|---|---|---|---|
| | Fluorescence Polarization | Enzyme | Radioimmunoassay |
| 1 | 1.08 | 0.96 | 28.9% |
| 2 | 0.69 | 0.78 | 34.6% |
| 3 | 1.15 | 1.01 | 26.5% |
| 4 | 2.25 | 1.56 | 15.6% |
| 5 | 0.98 | 0.67 | 30.5% | a T Uptake value of 1.0 is normal
a T Uptake value of 30% is normal. The fluorimetric measurement of the present invention is inversely proportional to $T_3$ Uptake values obtained using radioimmunoassay procedures.

As evidenced from the above specification and examples, the methods of the present invention provide a direct means for determining a T uptake value for a sample in a homogeneous assay system without the need for additional reagents, such as antibodies to thyroxine. In addition, the thyroxine-fluorescein conjugates employed in the present invention are relatively easy to produce and purify and are more stable than reagents employed in a T uptake assay employing enzyme inhibitor techniques. Furthermore, because this is a fluorescence assay, the sample size is generally significantly lower than that required in T uptake assays using conventional techniques.

The thyroxine-fluorescein conjugates useful as tracers in conjunction with the methods of the present invention may generally be prepared in accordance with conventional procedures. The following examples serve to illustrate the preparation of thyroxine-fluorescein conjugates that may be employed in the methods of the present invention. The symbol [CF] appearing in the structural formulas illustrating the compounds prepared in the following examples, represents a moiety of the formula:

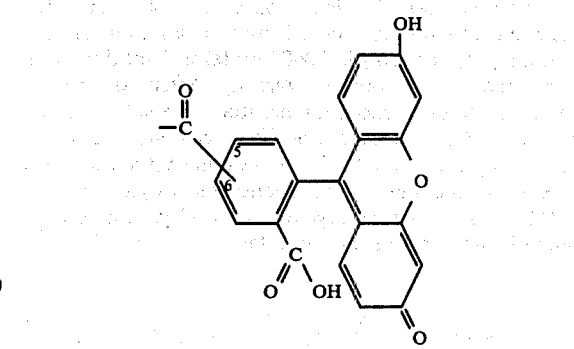

EXAMPLE 3

Preparation of N-Hydroxysuccinimide Active Ester of Carboxyfluorescein

To 83 mg (0.22 mmol) of 6-carboxyfluorescein dissolved in 2 ml of dimethylformamide was added 28 mg (0.24 mmol) of N-hydroxysuccinimide and 55 mg (0.27 mmol) of N,N'-dicyclohexylcarbodiimide. The reaction mixture was stirred at 0° C. under argon atmosphere for one hour and then maintained at 4° C. for 16 hours to yield a N-hydroxysuccinimide active ester of carboxyfluorescein having the formula:

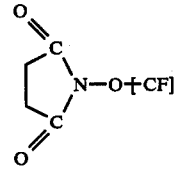

D-thyroxine sodium salt (100 mg, 0.00012 mole) is added with constant stirring to a solution of di-t-butyl dicarbonate (27 mg, 0.00012 mole) in 1 ml of dimethylformamide. After stirring two hours at room temperature the solvent is removed under high vacuum. The residue is dissolved in methanol and 1N HCl is added dropwise until a precipitate is formed. The solvent is decanted and the residue is dried under vacuum to yield 90 mg (82% yield) of N-t-butoxycarbonyl D-thyroxine having the formula:

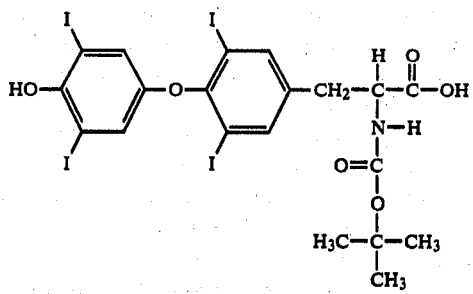

To a portion of the N-t-butoxycarbonyl D-thyroxine (51 mg, 0.00006 mole) dissolved in 1 ml of dimethylformamide is added N-hydroxysuccinimide (7 mg, 0.00006 mole) and N,N'-dicyclohexylcarbodiimide (15 mg, 0.00006 mole). The reaction mixture is stirred at room temperature for three hours after which time the reaction mixture is filtered into a solution of 1,3-diaminopropane (50 μl, 0.0003 mole) in 1 ml dimethylformamide with constant stirring. After stirring for fifteen minutes at room temperature, the solvent is removed and the residue is purified on a Whatman C18 reversed phase prep TLC plate eluting with a 80/19/1 mixture of methanol-water-acetic acid to yield 33 mg, (61% yield) of N-t-butoxycarbonyl D-thyroxine propylene diamine having the formula:

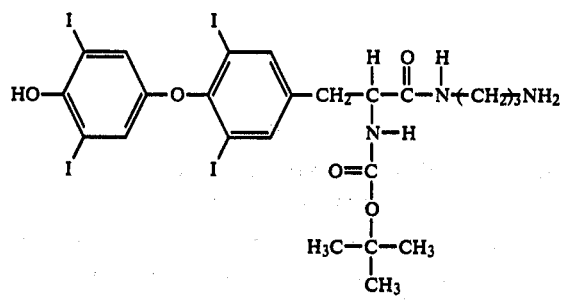

To a portion of the N-t-butoxycarbonyl D-thyroxine propylenediamine (10 mg, 0.00001 mole) dissolved in 1 ml of dimethylformamide is added N-hydroxysuccinimide active ester of a mixture of 5- and 6-carboxyfluorescein (5 mg, 0.00001 mole). The reaction mixture is stirred for thirty minutes at room temperature and the solvent is removed under vacuum. The residue is purified using a silica gel prep TLC plate eluting with a 9:1 mixture of methylene chloride:methanol to yield a mixture of N-t-butoxycarbonyl D-thyroxine propylenediamine carboxyfluorescein having the general formula:

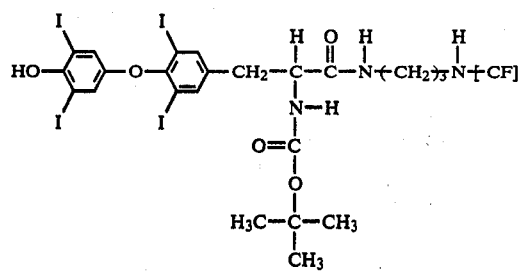

EXAMPLE 4

To a solution containing 5-aminovaleric acid (5.85 g, 0.05 mol) in 100 ml of 2% aqueous sodium hydroxide and 100 ml of dioxane was dropwise added a solution containing di-t-butyldicarbonate (10.9 g, 0.05 mol) in 40 ml of dioxane. The reaction mixture was stirred for 18 hours and then acidified to pH 3 using 1N hydrochloric acid. The acidified mixture was extracted three times with dichloromethane. The organic layers were combined, washed with water, and dried over sodium sulfate to yield 10.1 g (93.5% yield) of 5-(t-butoxycarbonylamino)valeric acid as a white crystalline solid.

To a portion of 5-(t-butoxycarbonylamino)valeric acid (0.434 g, 0.002 mol) was added N,N'-dicyclohexylcarbodiimide (0.412 g, 0.002 mol) and N-hydroxysuccinimide (0.25 g, 0.0022 mol) in 3 ml dichloromethane with constant stirring and the reaction was allowed to proceed for 18 hours to yield the N-hydroxysuccinimide active ester of 5-(t-butoxycarbonylamino)-valeric acid as an oily residue. To the oily residue was added L-thyroxine sodium salt pentahydrate (1.95 g, 0.0022 mol) in 30 ml of methanol.

The reaction was allowed to proceed for 18 hours after which time the reaction mixture was passed through an ion exchange resin column (Bio-Rad AG ®50W-X8 (H+ form) using methanol as the eluent.

The eluent was concentrated under vacuum to yield 1.96 g (90% yield) of intermediate of the formula:

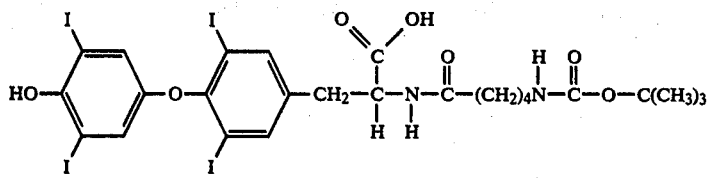

A portion of the intermediate (0.125 g, 0.00015 mol) was treated with trifluoroacetic acid (2.0 ml) for 30 minutes. The trifluoroacetic acid was removed via evaporation under reduced pressure and the resulting residue was dissolved in 1.5 ml of N,N'-dimethylformamide. The resulting solution was adjusted to a basic pH using triethylamine. To the resulting mixture was added N-hydroxysuccinimide active ester of carboxyfluorescein (75 mg, 0.000159 mol). The reaction was allowed to proceed for 18 hours. Diethylether was added to the reaction mixture to yield a precipitate which was purified via preparatory reverse phase TLC using a mixture of methanol:water:acetic acid (75:25:0.5) to yield 0.071 g of a thyroxine-6-carboxyfluorescein conjugate as an orange solid, having the formula:

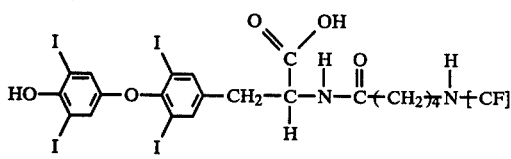

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A method for determining unsaturated thyroxine binding protein sites in a sample containing thyroxine binding proteins, comprising: (a) treating the sample with a composition comprising a nonfluorescent surfactant in a buffered medium having a pH greater than 7.0; (b) contacting the treated sample with a fluorescent labeled tracer wherein said fluorescent labeled tracer has a preferential binding affinity for thyroxine binding globulin, thereby forming a complex between the thyroxine binding proteins and fluorescent labeled tracer; and (c) determining the amount of complex formed utilizing fluorescence polarization techniques, as a measure of the unsaturated thyroxine binding protein sites in the sample.

2. A method according to claim 1 wherein the nonfluorescent surfactant is sodium dodecyl sulfate.

3. A method according to claim 2 wherein the pH of the buffered media is in the range of 8.0–9.0.

4. A method according to claim 3 wherein the buffer is sodium bicarbonate.

5. A method according to claim 2 wherein the buffered media comprises triethylenediamine in a phosphate buffer.

6. A method according to claim 1 wherein the fluorescent labeled tracer comprises a thyroxine-fluorescein conjugate.

7. A method according to claim 6 wherein the thyroxine-fluorescein conjugate is a compound of the formula:

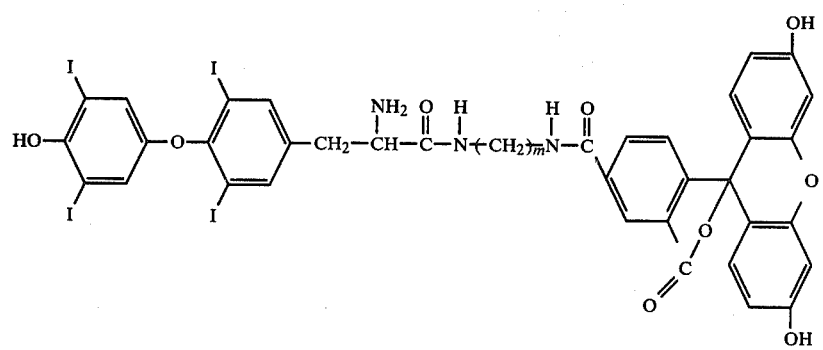

or

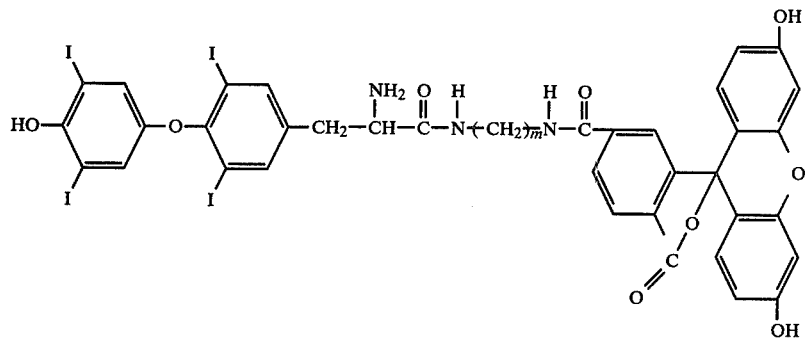

wherein m is an integer of from 2 to 8.

8. A method according to claim 7 wherein m is an integer of from 2 to 4.

9. A method according to claim 8 wherein m is 3.

10. A method as in any of claims 1–9 wherein steps (a) and (b) are conducted simultaneously.

* * * * *